United States Patent
Björling et al.

(10) Patent No.: US 8,233,983 B2
(45) Date of Patent: Jul. 31, 2012

(54) IMPLANTABLE HEART STIMULATOR AND METHOD FOR OPERATION THEREOF

(75) Inventors: Anders Björling, Solna (SE); Nils Holmström, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 1123 days.

(21) Appl. No.: 11/793,478

(22) PCT Filed: Dec. 17, 2004

(86) PCT No.: PCT/SE2004/001924
§ 371 (c)(1),
(2), (4) Date: Feb. 12, 2008

(87) PCT Pub. No.: WO2006/065184
PCT Pub. Date: Jun. 22, 2006

(65) Prior Publication Data
US 2008/0281373 A1    Nov. 13, 2008

(51) Int. Cl.
*A61N 1/08*     (2006.01)
*A61N 1/37*     (2006.01)

(52) U.S. Cl. .......................................... 607/28; 607/27

(58) Field of Classification Search ................ 607/27, 607/28
See application file for complete search history.

(56) References Cited

U.S. PATENT DOCUMENTS

| | | |
|---|---|---|
| 6,317,633 B1 | 11/2001 | Jorgenson et al. |
| 6,456,882 B1 | 9/2002 | Schloss |
| 6,714,819 B1 | 3/2004 | Sloman |
| 2003/0083708 A1* | 5/2003 | Bradley et al. ............. 607/27 |
| 2005/0159785 A1* | 7/2005 | Rueter ........................ 607/28 |

FOREIGN PATENT DOCUMENTS
WO    WO 2004/039447    5/2004
* cited by examiner

*Primary Examiner* — Tammie K Heller

(57) ABSTRACT

In an implantable heart stimulator and a method for operation thereof, stimulation pulses are delivered to a heart. The amplitude of the delivered stimulation pulses can be selectively set. For setting the amplitude, threshold searches are performed at selected time intervals. Each threshold search determines a threshold value required for achieving capture. The amplitudes of the respective stimulation pulses are set to a value that exceeds the determined threshold value by a safety margin. The safety margin is selected as a function of the selected time intervals.

18 Claims, 4 Drawing Sheets

Capture threshold v.s. time after implantation, inclining safety margin

Capture threshold v.s. time after implantation, stepped safety margin

IMPLANTABLE HEART STIMULATOR AND METHOD FOR OPERATION THEREOF

BACKGROUND OF THE INVENTION

1. Field of the Invention

The present invention relates to implantable heart stimulators, such as pacemakers, defibrillators, cardioverters, implantable cardioverter-defibrillators ("ICDs"), and similar cardiac stimulation devices that also are capable of monitoring and detecting electrical activities and events within the heart.

2. Description of the Prior Art

Implantable pacemakers generate electrical stimulation pulses and deliver such stimulation pulses to atrial and/or ventricular muscle tissue of a patient's heart at a prescribed rate and/or rhythm when, through disease or other cause, the heart is not able to maintain the prescribed heart rate or rhythm on its own. When the delivered electrical stimuli are of sufficient energy, they cause the cardiac muscle tissue to depolarize, and therefore contract, thereby forcing the heart rate or rhythm to track the delivery of the electrical stimuli. When the delivered electrical stimuli are of insufficient energy, depolarization does not occur, and the heart rate or rhythm is not controlled by the pacemaker. Hence, for the pacemaker to perform its intended function, it is important that the delivered electrical stimuli is of sufficient energy to depolarize the cardiac tissue.

The depolarization and ensuing contraction of the heart in response to a delivered cardiac stimulation pulse is generally referred to in the art as "capture". Consequently, the term "non-capture" denotes the condition when a delivered stimulation pulse does not result in depolarization and contraction. When detecting capture, a sensing circuitry checks for the depolarization of a cardiac chamber following and in response to a delivered stimulation pulse. Such a depolarization as a result of a delivered stimulation pulse is also referred to as an "evoked response" (ER) of that chamber. Furthermore, the evoked response is detected during a selected time period following the delivery of a stimulation pulse. Such a time period is generally referred to as an "evoked response window".

The energy of the electrical stimuli generated by an implanted pacemaker is derived from the energy stored in the pacemaker power source or battery. The pacemaker battery has a limited amount of energy stored therein, and the generation of electrical stimuli represents by far the greatest drain of such energy.

The amount of energy needed to effectuate capture is known as the capture "threshold", and electrical stimuli of energy less than the capture threshold do not bring about capture, while electrical stimuli of energy greater than the capture threshold do bring about capture.

A capture threshold search normally begins at a desired starting point (either a high energy level or the level at which capture is currently occurring) and the energy level is decreased until capture is lost. The value at which capture is lost is known as the capture threshold. Thereafter, in order to secure capture, a safety margin is added to the capture threshold to arrive at the energy content of the stimulation pulse. One of the key issues is to choose the safety margin such that it guarantees capture and at the same time provides adequate energy savings and does not cause pectoral stimulation and/or sensation.

In order to preserve this limited energy and to prolong the life of the battery, it is known in the art to adjust the energy content of the delivered electrical stimuli so that it is just sufficient to cause capture, with an appropriate safety margin. One such method is described in U.S. Pat. No. 6,714,819, wherein a calculation of the safety margin is made based on a measured variation of the threshold value. However, when such calculation are used the adjustment of the safety margin is not immediate, but dependent on previous threshold values. Hence, there will be a delay in the adjustment of the safety margin, if a rapid change suddenly occurs after a period of substantially constant threshold values.

Capture detection may occur on a beat-by-beat basis or on a sampled basis. In autocapture systems where a beat-by-beat capture verification is provided by the pacemaker, a fixed safety margin has generally been proven to be adequate. If a threshold increase occurs, the pacemaker responds by increasing the output amplitude and re-finding the capture threshold, to which the safety margin is added. This method reduces the energy consumption in the stimulation device by adding the lowest possible safety margin that the pacemaker allows.

For example, in a cardiac stimulation device arranged for biventricular stimulation, the stimulation threshold and the evoked response, or depolarization of the muscle tissue, are measured both in the first and the second stimulated ventricle, which normally is the left and the right ventricle, respectively. In many cases, there is an intraventricular delay between the stimulation pulses delivered to the first and the second ventricle. When this delay is short, e.g. less than approximately 60 ms, the stimulation pulse of the secondary ventricle can interfere with the capture detection in the primary ventricle. This interference makes the evoked response detection in the primary ventricle difficult.

Therefore, capture is not always verified on a beat-by-beat basis in the primary ventricle, but rather after certain programmable time intervals, e.g. 15 min. or 1000 heartbeats. At these instants, the evoked response (ER) window for the first ventricle is normally made clear from disturbing stimulation pulses in other places of the heart by a temporarily changed timing pattern.

To ensure capture between these threshold verifications, a sufficient, fixed safety margin is introduced for the first ventricle. This safety margin is normally higher than the safety margin in the second ventricle to account for the fact that the capture verification is not performed on a beat-by-beat basis in the first ventricle.

However, capture verification requires additional processing time and corresponding consumption of battery energy.

SUMMARY OF THE INVENTION

An object of the present invention to eliminate, or at least alleviate, the described problems associated with a heart stimulator.

The invention is based on determining the safety margin in correspondence with the duration of a selectable interval or period between two successive threshold searches or threshold updates. This period can e.g. be a predetermined time interval or a predetermined number of heart beats. This advantageously facilitates the use of a lower safety margin without causing an increased risk for loss of capture (LOC). Lowering the safety margin without causing LOC, decreases the energy consumption and increases the life of the pacemaker.

By adjusting the safety margin such that the energy of the electrical stimuli is normally always greater than the capture threshold, but not too much greater, the limited energy of the pacemaker battery may thus be preserved. The battery energy is preserved because: electrical stimuli of insufficient energy to cause capture (electrical stimuli below threshold), which stimuli represent wasted energy, are rarely generated; and electrical stimuli of excessive energy (not only representing wasted energy, but also energy that may disadvantageously cause pectoral stimulation and/or sensation), are also rarely generated.

The above object is achieved according to the present invention by an implantable heart stimulator having a pulse generator for delivering stimulation pulses of varying amplitudes, a first electrode lead connected to said pulse generator for conducting delivered pulses to the heart, sensing circuitry that detects capture or non-capture of the heart in response to the delivered pulses, and a programmable processor for evaluating the detected capture and non-capture and for controlling the timing and amplitude of the stimulation pulses. The processor is programmed to search and determine a threshold value for the pulse amplitude required for effectuating capture. The searches are performed at least at certain points in time, which are separated by selected period or a predetermined time period. The processor is also programmed to set the amplitudes of stimulation pulses to a value exceeding the determined threshold value by a predetermined margin, which is a function of the selected periods. The predetermined margin is in the following referred to as the safety margin.

The above object also is achieved according to the present invention provides a method of determining the amplitude of a stimulation pulse for stimulating a human heart using an implantable heart stimulator. This method includes the steps of delivering successive stimulation pulses to a first ventricle of the heart, each stimulation pulse having a set pulse amplitude, performing threshold searches for determining a threshold value of the pulse amplitude required for effectuating capture, wherein the interval between successive such threshold searches is a selected period, and setting the pulse amplitudes of the stimulation pulses to a value exceeding the threshold value by a predetermined margin. The predetermined margin is selected as a function of the selected period.

One advantage of the present invention is the enabled use of a safety margin, which is adapted to the interval between two capture threshold searches. In other words, a lower safety margin can be used without an increased risk for LOC, compared to the use of a fixed safety margin, even when there is a large time interval between the threshold searches and/or the capture threshold changes rapidly. The present invention also provides for improved Cardiac Resynchronization Therapy (CRT), as an LOC occurs less frequently, which also gives a lower energy consumption of the pacemaker.

According to further embodiments, implantable heart stimulators according to the present invention can be arranged for biventricular heart stimulation. Then, the heart stimulator comprises a second electrode lead connected to the pulse generator for conducting stimulation pulses to the second ventricle of the heart. During one heart-beat cycle, a first stimulation pulse is generally delivered to the first ventricle of the heart via a first cardiac lead, and a second stimulation pulse is shortly thereafter delivered to the second ventricle of the heart via a second cardiac lead. Moreover, the search and determination of a threshold value, for the pulse amplitude required for effectuating capture, is performed for said first ventricle at least at predetermined time intervals, and the amplitude is set to a value exceeding said determined threshold value by the predetermined margin.

In a biventricular heart stimulator, where capture detections are not performed on a beat-to-beat basis in the first ventricle, the fixed safety margin is normally set to a higher value, as compared to the safety margin used for the second ventricle. Thereby, the risk for LOC between two preprogrammed threshold searches is reduced. In other words, the heart stimulator with a fixed safety margin must take into account a rapid threshold increase, which might occur between two successive threshold searches separated by a larger time interval. Therefore, the fixed safety margin is normally set as high as 0.8 V for the first ventricle. On the other hand, in a biventricular heart stimulator arranged according to the invention, the time interval between two threshold searches is known and therefore a substantially lower safety margin can be used. An exemplary safety margin in a heart stimulator according to the invention could be less than 0.1 V.

The first time period following implantation of an implantable heart stimulator is often referred to as the acute period. During this period, the capture threshold is known to rise and reach a maximum after a period of approximately 2 weeks. Thereafter, the capture threshold generally decreases to a plateau after approximately another 3 weeks. The threshold rise can be as high as 3 V, as the result of a threshold increase rate of up to about 10 mV/hour.

Advantageously, the heart stimulator is arranged such that the determined margin is a function of the predetermined time interval during a selected period of time only, e.g. during the acute period or any other period during which the capture threshold is expected to increase. The selected period of time is preferably between 4 and 20 weeks. Thereby, use of the invention can be limited to a time period when an increased change in the capture threshold is expected. Preferably, this time period is set by a physician according to the specific needs of a particular patient.

Advantageously, the function for determining the predetermined margin on the basis of the predetermined time interval is a linear function, e.g. expressed as $k*T$, where k is a constant and T is said predetermined time interval. This provides a safety margin that results in a stimulation pulse which is larger than an expected increase of the stimulation threshold margin of a patient's heart between two successive threshold searches, while at the same time being as low as possible without increasing the risk for LOC. Preferably, k is between 5-50 mV/hour, or more preferably between 10-30 mV/hour. Furthermore, T is preferably set to between 4 and 24 hours, and more preferably to between 6 and 10 hours.

According to another embodiment of the present invention, the function for determining the predetermined margin on the basis of the predetermined time interval takes into account a possible expected increase in the actual threshold. In one example, said function is expressed as:

$$((kT-m)/T)(t+m)$$

wherein k is a first constant,
T is said predetermined time interval,
t is the elapsed time since the latest threshold search, and
m is a second constant.

m is preferably chosen such that a safety margin large enough to ensure a minimum risk for LOC due to temporary, rapid fluctuations of the capture threshold value is provided. Preferably, this value is between 10-500 mV, and more preferably between 50-100 mV. Moreover, k is selected such that $k*T-m$ is larger than an expected long term evolvement or change of the capture threshold over time.

In other words, and according to this embodiment, the safety margin is arranged to increase during said time period T in accordance with an expected or anticipated possible rise in the capture threshold. The use of such a function for setting the safety margin is advantageous in that only a minimum amount of excessive stimulation pulse energy, i.e. wasted energy, is spent at the beginning of each time interval between two successive threshold searches, as compared to when the stimulation pulse is set to a constant value during the whole time interval between two successive threshold searches.

Advantageously, the processing means is arranged such that k and/or T are/is selectable, i.e. it is possible to change the interval between e.g. two threshold searches. This enables a most dynamic programming of the heart stimulator, without increasing the risk for LOC. Hence, the parameters of the heart stimulator can be adjusted by a physician according to what is most appropriate for a particular patient.

According to other embodiments of the present invention, the selected period can be the interval between two successive verifications of capture TC, for instance in the first ventricle. These are normally separated by a shorter time interval, as compared to the interval between two successive threshold searches. In this embodiment, the same functions as those described above can be used, wherein T then would be exchanged for TC. Preferably, k is chosen within the range of 10-50 mV/hour.

DESCRIPTION OF THE PREFERRED EMBODIMENTS

The following is a description of preferred embodiments for practicing the invention. This description is not to be considered in a limiting sense, but is made merely for the purpose of describing the general principles of the invention. Thus, although a biventricular heart stimulator with atrial and ventricular sensing and stimulating functionalities will be described, the invention is also applicable to univentricular stimulators, as well as to stimulators without atrial sensing and/or stimulation.

Figure 1:
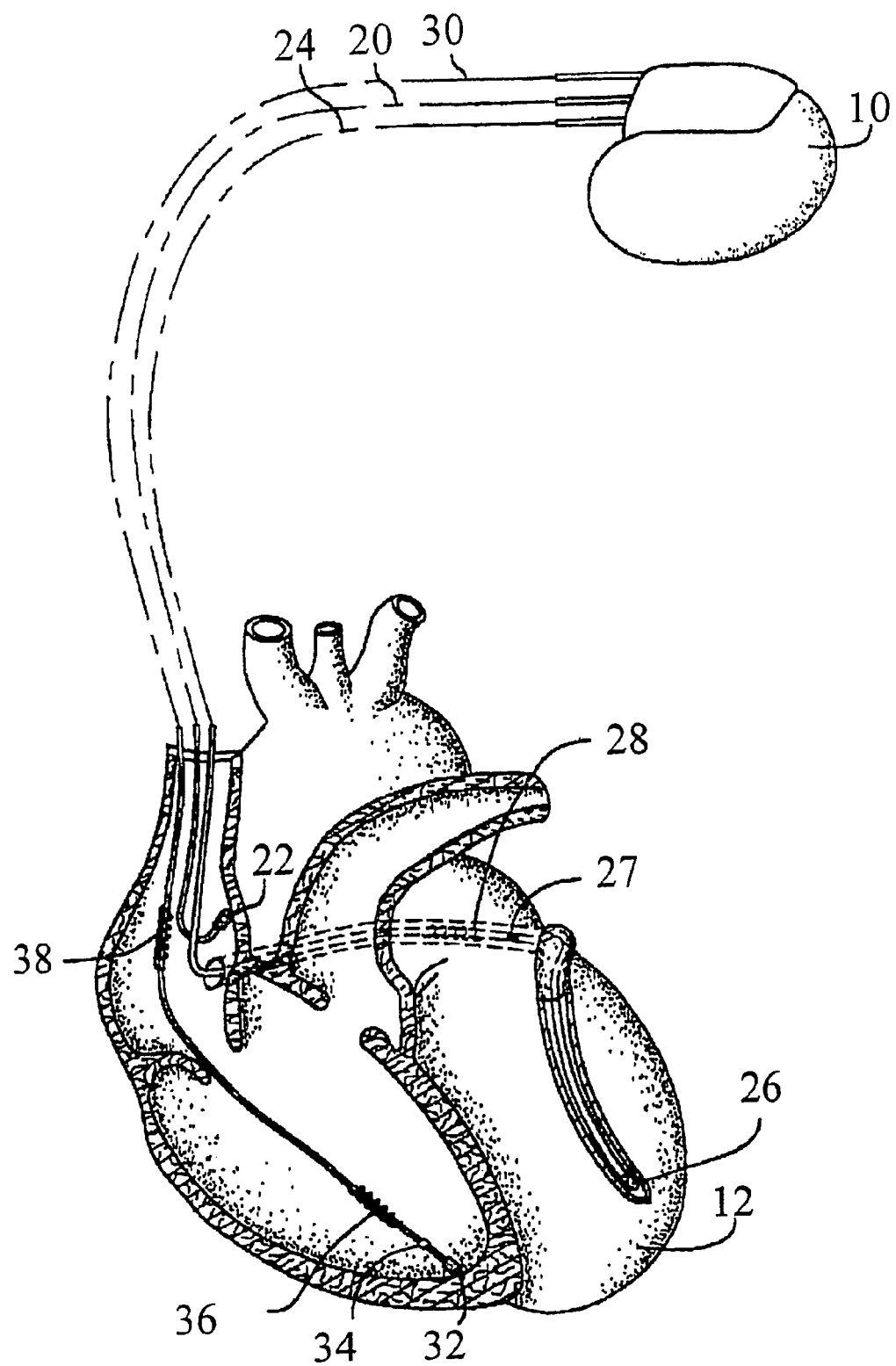
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation (and shock therapy). In order to sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

In order to sense left atrial and ventricular cardiac signals and to provide left-chamber pacing therapy, the stimulation device 10 is coupled to a "coronary sinus" lead 24 designed for placement in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left lateral vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, refer to U.S. patent application Ser. No. 15 09/457,277, filed Dec. 8, 1998, titled "A Self-Anchoring, Steerable Coronary Sinus Lead" (Pianca et. al); and U.S. Pat. No. 5,466,254, titled "Coronary Sinus Lead with Atrial Sensing Capability" (Helland), which patent application and patent are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior versa cava. Accordingly, the right ventricular lead 30 is capable of receiving cardiac signals, and delivering stimulation in the form of pacing and shock therapy to the right ventricle.

Figure 2:
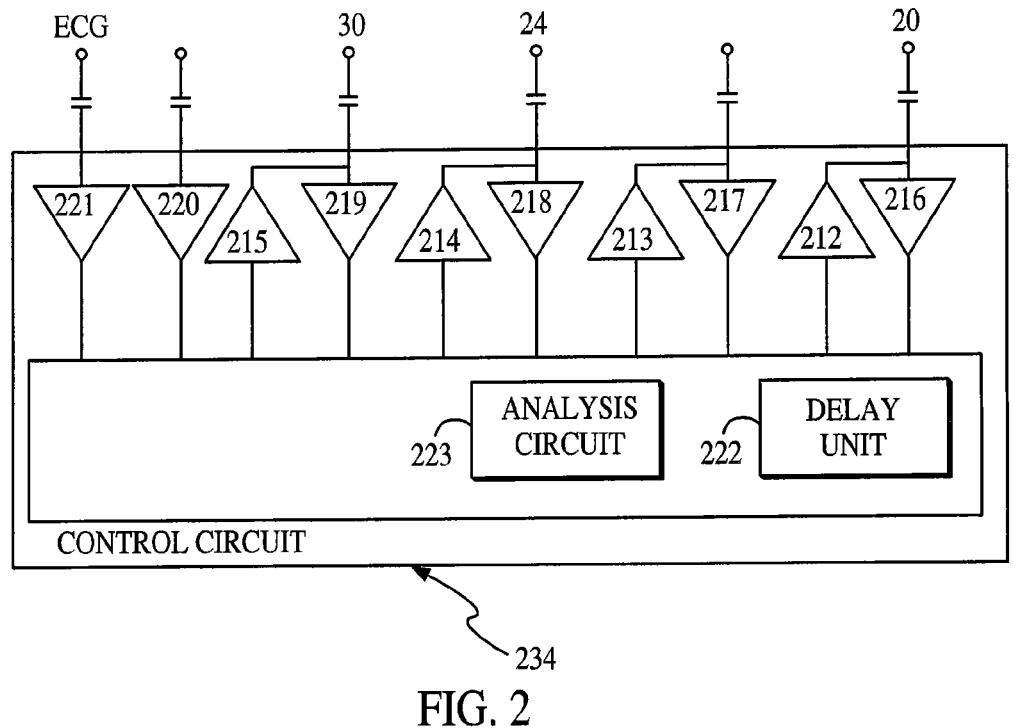
FIG. 2 is a functional block diagram of the multi-chamber implantable stimulation device of FIG. 1, illustrating the basic elements that provide cardioversion, defibrillation and/or pacing stimulation in four chambers of the heart.

FIG. 2 shows a block diagram of a control circuit 234 used in the pulse generator 10. The control circuit includes pacing pulse output circuits 212, 213, 214, 215 for delivering stimulation pulses to heart electrode leads 20, 24, 30. The control circuit 234 is adapted for a general pacing system configuration where right and left atria as well as right and left ventricles are paced and sensed. However, in many cases the pacing system comprises one atrial heart electrode lead and two ventricular heart electrode leads. The control circuit 234 further includes sense amplifiers and detectors 216, 217, 218, 219 for sensing atrial and ventricular activity respectively. Sense amplifiers 220 and 221 are used for sensing an intracorporal ECG signal from locations outside of the heart. The control circuit 234 also has delay unit 222 that delivers the stimulating pulses to the first and second ventricular heart electrode leads 24, 30 within the same heart cycle with a delay between the stimulating pulses. This delay may be varied.

Furthermore, the control circuit 234 in the present invention includes an analysis circuit 223 that analyzes the intracorporal ECG signal obtained via sense amplifiers 220 and 221. The analysis may include QRS duration, QRS morphology, duration of most significant deflection, or ST segment visibility. From the analysis it can be determined if there is capture on both ventricles via heart electrode leads 24 and 30, or if there is loss on one or both of the ventricles. If there is loss on both ventricles, then no intracorporal evoked QRS will be present and a back-up pacing pulse to one or both ventricles will be emitted by pacing pulse output circuits 214, 215.

Figure 3:
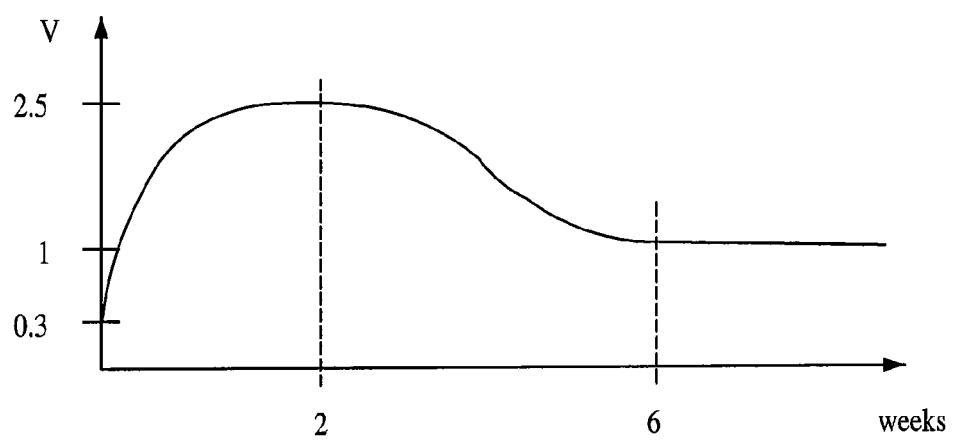
FIG. 3 is a schematic illustration of the increase in capture threshold during the acute-period.

FIG. 3 schematically shows a typical change of the capture threshold during the acute period, i.e. the period following an implantation of a heart stimulator. During the first approximately two weeks there is a rapid increase in the capture threshold, which typically amounts to up to 3 V. This equals a threshold increase of about 10 mV/h. Thereafter, the capture threshold decreases and reaches a plateau of about 1 V after approximately another 4 weeks. The duration and size of the threshold variation differs from patient to patient and is related to a variety of physiologic and pharmacologic factors. As an example, the use of steroids at the implantation can normally reduce the rise of the capture threshold, such that it reaches the plateau without a previous substantial decrease of the threshold. Sleeping or eating can cause a rise of the capture threshold with about 30-40%. The same is true for some pharmacological substances, e.g. flecainide which can cause a rise as large as 200%. More documentation about capture threshold rise due to physiologic and pharmacological factors can be found in medical literature.

Figure 4:
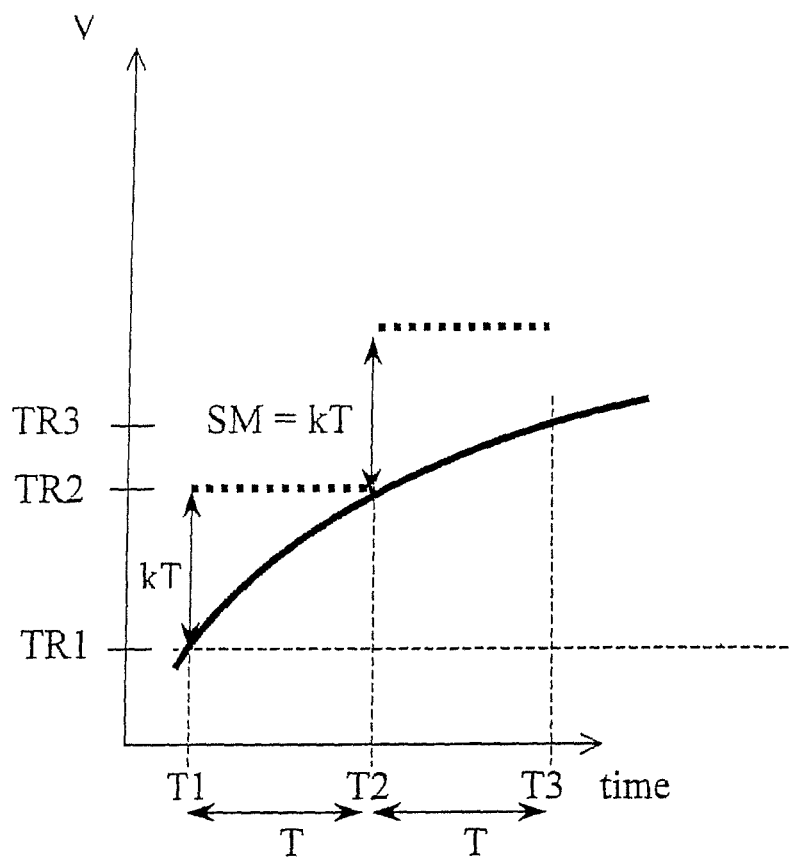
FIG. 4 is a schematic illustration of a first design to adapt the stimulation amplitude at increasing threshold in accordance with an embodiment of the invention.

FIG. 4 is a schematic illustration of a first safety margin determination according to an embodiment of the invention. The graph shows a capture threshold increase over time between three threshold searches T1, T2 and T3, wherein the time T between successive threshold searches is e.g. 8 hours. The increase is vastly exaggerated for illustration purposes. After each threshold search, a capture threshold TR1, TR2 and TR3, respectively, is determined. When a capture threshold has been determined, a stimulation voltage is set to a voltage equaling the latest determined capture threshold plus a safety margin.

In this embodiment, the safety margin is k*T, where k is a constant which preferably in the range of 5-50 mV/h, and more preferably between 10 and 30 mV/h. Advantageously, k is chosen such that the resulting safety margin is larger than temporary fluctuations and a long term increase of the capture threshold between two consecutive threshold searches. Consequently, the stimulation pulse voltage is TR1+kT after the first 35 threshold search, TR2+kT after the second, and TR3+kT after the third. Since the time interval between two successive threshold searches in this example is 8 hours and a threshold rise during the acute period is normally about 10 mV/hour, the safety margin (k*T) should be at least 0.08 V during this period. This is substantially less than the fixed safety margin of normally 0.3 V, which is frequently used today.

Figure 5:
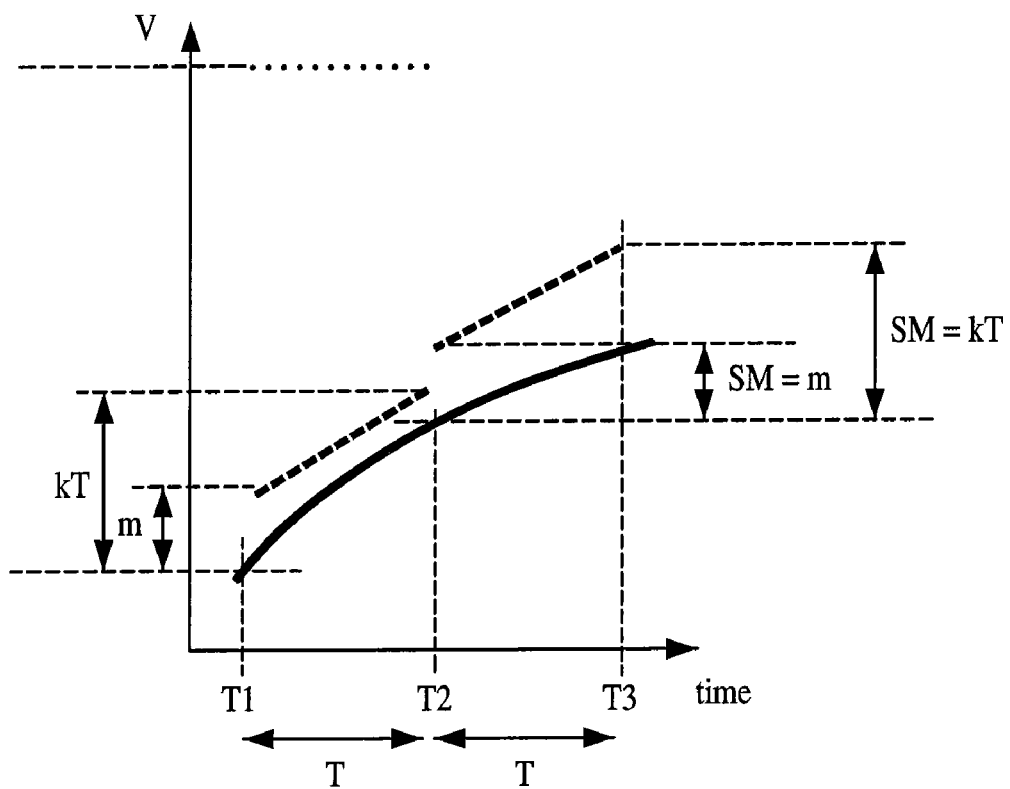
FIG. 5 is a schematic illustration of a second design to adapt the stimulation amplitude in accordance with another embodiment of the invention.

FIG. 5 is a schematic illustration of a second example of safety margin determination according to the invention. In this case, the conditions are the same, i.e. capture threshold increase, threshold determinations TR1, TR2 and TR3, and time between successive threshold searches T, as was explained in relation to FIG. 4. The only difference is the determination of the threshold margin. Instead of determining a constant safety margin, to be applied for the whole time period T between two successive threshold searches, the safety margin varies during the time period T.

Thus, directly after a capture threshold has been determined, the stimulation pulse voltage is set to the latest threshold value plus a minimum safety margin m. Preferably, the minimum safety margin m is chosen such that it is larger than a temporary fluctuation of the capture threshold, e.g. to a value between 10 and 50 mV. Thereafter, the safety margin is increased, e.g. linearly, such that the stimulation voltage equals the capture threshold plus k*T at the time when the next threshold search is due. The safety margin can be expressed as:

$$((kT-m)/T)(t+m)$$

where t is the time elapsed since the latest threshold search and k, T, m is defined as explained above.

According to particular embodiments of the present invention, the safety margin can be determined using different functions during different periods of time. As an example, the safety margin could be equal to ((kT−m)/T)(t+m) during the expected threshold rise occurring in the first couple of weeks after implantation, and then be changed to equal k*T. The second function k*T could then be used during the remaining weeks of the acute period, during the remainder of the stimulator life, or until the safety margin is deliberately set to a specific value.

Preferably, k and T, and m when applicable, are all selectable within a respective suitable interval. This enables an adaptation of the safety margin to the particular need of each patient.

Although the invention disclosed herein has been described by means of specific embodiments and applications thereof, numerous modifications and variations could be made therein by those skilled in the art without departing from the scope of the invention. For example, and as stated above, although the heart stimulator described herein is arranged for biventricular stimulation, the invention is also applicable to univentricular stimulation.

We claim as our invention:

1. An implantable heart stimulator comprising:
   a pulse generator that emits stimulation pulses each having an amplitude, said amplitude being variable;
   at least one electrode lead connected to said pulse generator and configured to conduct pulses emitted by said pulse generator to a heart;
   sensing circuitry connected to said at least one electrode lead to receive a signal therefrom indicative of electrical cardiac activity, said sensing circuitry detecting capture or non-capture of the heart in response to the pulses delivered by said at least one electrode lead;
   a processor connected to said sensing circuitry, said processor being configured to evaluate the capture and non-capture detection by said sensing circuitry and to control said pulse generator to set a timing and said amplitude of said stimulation pulses;
   said processor being configured to conduct a search to determine a threshold value for a pulse amplitude required for achieving capture, said processor being configured to conduct said search at each of successive points in time respectively separated by a selected time period, and to set said amplitude of said stimulation pulses to a value exceeding said threshold value by a predetermined margin, and to set said predetermined margin as a function of said selected time period expressed as k*T, wherein k is a first constant and T is selected said time period; and
   a housing configured for implantation in a patient, containing said pulse generator, said sensing circuitry and said processor.

2. An implantable heart stimulator as claimed in claim 1 wherein said at least one electrode lead is a first electrode lead configured to deliver said stimulation pulses to a first ventricle of the heart, and wherein said implantable heart stimulator comprises:
   a second electrode lead connected to said pulse generator and configured to conduct said stimulation pulses to a second ventricle of the heart;
   said processor being configured to control said pulse generator to cause, during each cardiac cycle, a first stimulation pulse to be delivered first to said first ventricle via said first electrode lead and a second stimulation pulse to be delivered subsequently to said second ventricle via said second electrode lead; and
   said processor being configured to conduct said search to determine said threshold value for said first ventricle at least at said successive points in time.

3. An implantable heart stimulator as claimed in claim 1 wherein said processor is configured to select said selected time period to have a duration selected from the group consisting of a selected time interval and a selected number of cardiac cycles of the heart.

4. An implantable heart stimulator as claimed in claim 1 wherein said processor is configured to select said predetermined margin as a function of said time period to be effective only for a selected effective time duration.

5. An implantable heart stimulator as claimed in claim 4 wherein said processor is configured to select said effective time duration to be between four and twenty weeks.

6. An implantable heart stimulator as claimed in claim 1 wherein said processor is configured to select said predetermined margin to increase linearly within said selected time period according to the following equation:

$$((kT-m)/T)(t+m)$$

wherein k is the first constant, T is said selected time period, t is an elapsed time from a latest, previous point in time among said successive points in time, at which a latest, previous search was conducted, and m is a second constant.

7. An implantable heart stimulator as claimed in claim 6 wherein said processor is configured to employ a value for m in a range between 10 and 500 mV.

8. An implantable heart stimulator as claimed in claim 7 wherein said processor is configured to employ a value m in a range between 50 and 100 mV.

9. An implantable heart stimulator as claimed in claim 6 wherein said processor is configured to employ a value for k in a range between 5 and 50 mV/hour.

10. An implantable heart stimulator as claimed in claim 9 wherein said processor is configured to employ a value for k in a range between 10 and 30 mV/hour.

11. An implantable heart stimulator as claimed in claim 6 wherein said processor is configured to employ a value for T in a range between 4 and 24 hours.

12. An implantable heart stimulator as claimed in claim 6 wherein said processor is configured to employ a value for T in a range between 6 and 10 hours.

13. An implantable heart stimulator as claimed in claim 6 wherein said processor is configured to employ a value for m in a range between 10 and 500 mV, and a value for k in a range between 5 and 50 mV/hour, and a value for T in a range between 4 and 24 hours.

14. An implantable heart stimulator as claimed in claim 6 wherein said processor is configured to select at least one of k, T and m to be a value within a respective range of values.

15. A method for determining an amplitude of a stimulation pulse for stimulating a human heart using an implantable heart stimulator, comprising the steps of:

delivering successive stimulation pulses to a ventricle of the heart, each stimulation pulse having a selectively set pulse amplitude;

in a processor, automatically performing successive threshold searches respectively separated by a selected time period and in each search determining a threshold value of the pulse amplitude required to achieve capture of the heart; and from said processor, setting said pulse amplitude of the stimulation pulses after each search to a value exceeding said threshold value by a predetermined margin, and selecting said predetermined margin as a function of said selected time period expressed as k*T, wherein k is a first constant and T is said selected time period, and selecting a value for k within a predetermined range of values.

16. A method as claimed in claim 15 comprising selecting said selected time period as being a selected time duration or a selected number of cardiac cycles of the heart.

17. A method as claimed claim 15 comprising setting said predetermined margin according to the following equation:

$$((kT-)/T)(t+m)$$

wherein k is the first constant, m is a second constant, T is said selected time period, and t is an elapsed time from a latest, previous point in time among said successive points in time, at which a latest, previous threshold search was conducted, and selecting respective values for k and m within respective ranges of values.

18. A method as claimed in claim 17 comprising, after selecting and setting respective values for k, T and m, changing at least one of the set values for k, T or m to a new value upon conducting a subsequent search.

* * * * *